(12) United States Patent
Horiuchi et al.

(10) Patent No.: US 10,709,404 B2
(45) Date of Patent: Jul. 14, 2020

(54) RADIOGRAPHY SUPPORT DEVICE, RADIATION DETECTION DEVICE, RADIOGRAPHY APPARATUS, RADIOGRAPHY SUPPORT METHOD, AND RADIOGRAPHY SUPPORT PROGRAM

(71) Applicant: FUJIFILM Corporation, Tokyo (JP)

(72) Inventors: Hisatsugu Horiuchi, Kanagawa (JP);
Sho Shimizukawa, Kanagawa (JP);
Masateru Tateishi, Kanagawa (JP);
Shinsuke Noguchi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 101 days.

(21) Appl. No.: 16/197,750

(22) Filed: Nov. 21, 2018

(65) Prior Publication Data
US 2019/0183448 A1 Jun. 20, 2019

(30) Foreign Application Priority Data
Dec. 14, 2017 (JP) .................................. 2017-239745

(51) Int. Cl.
*A61B 6/00* (2006.01)
*A61B 5/00* (2006.01)

(52) U.S. Cl.
CPC .......... *A61B 6/5294* (2013.01); *A61B 6/4233* (2013.01); *A61B 6/461* (2013.01); *A61B 6/5205* (2013.01); *A61B 6/542* (2013.01); *A61B 6/587* (2013.01); *A61B 6/589* (2013.01)

(58) Field of Classification Search
CPC .................................... A61B 6/00; A61B 5/00
USPC ........................................................ 382/132
See application file for complete search history.

(56) References Cited

U.S. PATENT DOCUMENTS

2012/0018641 A1* 1/2012 Watanabe .............. A61B 6/563
250/354.1

FOREIGN PATENT DOCUMENTS

JP 2012-24231 A 2/2012
JP 2014-198271 A 10/2014

* cited by examiner

*Primary Examiner* — Abolfazl Tabatabai
(74) *Attorney, Agent, or Firm* — Birch, Stewart, Kolasch & Birch, LLP

(57) ABSTRACT

A radiography support device that supports imaging of an object with a radiation detection panel in which a plurality of pixels are two-dimensionally arranged and which detects radiation emitted from a radiation source, includes: a first reading control unit that reads first pixel signals from at least some of the plurality of pixels in a state in which the radiation is not emitted from the radiation source and a state in which the object is placed on the radiation detection panel; a first arithmetic unit that calculates a position of the object with respect to the radiation detection panel based on the first pixel signals; and a notification processing unit that performs a notification process in a case in which the position of the object is out of a predetermined range.

17 Claims, 12 Drawing Sheets

RADIOGRAPHY SUPPORT DEVICE, RADIATION DETECTION DEVICE, RADIOGRAPHY APPARATUS, RADIOGRAPHY SUPPORT METHOD, AND RADIOGRAPHY SUPPORT PROGRAM

CROSS-REFERENCE TO RELATED APPLICATIONS

This application claims the benefit of Japanese Patent Application JP 2017-239745, filed Dec. 14, 2017, the entire content of which is hereby incorporated by reference, the same as if set forth at length.

BACKGROUND OF THE INVENTION

1. Field of the Invention

The present invention relates to a radiography support device, a radiation detection device comprising the radiography support device, a radiography apparatus comprising the radiography support device, a radiography support method, and a computer readable medium storing a radiography support program.

2. Description of the Related Art

A radiography apparatus using radiation (for example, X-rays) has been known. The radiography apparatus includes a radiation detection device that detects radiation transmitted through a patient that is an object and generates a radiographic image signal based on the detected radiation and a control device that controls the radiation detection device.

Examples of the radiation detection device include a stationary type that is fixed to an imaging table provided in a dedicated imaging room and a portable type in which a radiation detection panel is accommodated in a portable housing.

The portable radiation detection device includes a radiation detection panel that is called an electronic cassette and is also called a flat panel detector (FPD), a memory that temporarily stores a radiographic image signal, and a communication unit that transmits the radiographic image signal to a control device.

In the radiography apparatus, it is necessary to accurately adjust the positional relationship between the object and the radiation detection panel in order to record an appropriate radiographic image.

JP2012-024231A discloses a radiography apparatus that detects the position of an object with respect to a radiation detection panel with a pressure sensor or a temperature sensor which is provided in the radiation detection panel.

JP2014-198271A discloses a radiography apparatus that detects the position of an object with respect to a radiation detection panel with a pressure sensor which is provided in a lower part of a top plate of an imaging table.

SUMMARY OF THE INVENTION

The X-ray imaging apparatuses disclosed in JP2012-024231A to JP2014-198271A require a dedicated sensor, such as a pressure sensor, in order to detect the position of the object. Therefore, the manufacturing costs of the apparatus increase. For example, in a case in which a dedicated sensor is added to the radiation detection panel, flexibility in the design of the radiation detection panel is reduced or it is necessary to consider the influence of the sensor on a captured image.

The invention has been made in view of the above-mentioned problems and an object of the invention is to provide a radiography support device that can calculate the position of an object with respect to a radiation detection panel, without adding a dedicated sensor to the radiation detection device, a radiation detection device comprising the radiography support device, a radiography apparatus comprising the radiography support device, a radiography support method, and a radiography support program.

According to the invention, there is provided a radiography support device that supports imaging of an object with a radiation detection panel in which a plurality of pixels are two-dimensionally arranged and which detects radiation emitted from a radiation source. The radiography support device comprises: a first reading control unit that reads first pixel signals from at least some of the plurality of pixels in a state in which the radiation is not emitted from the radiation source and a state in which the object is placed on the radiation detection panel; a first arithmetic unit that calculates a position of the object with respect to the radiation detection panel on the basis of the first pixel signals; and a notification processing unit that performs a notification process in a case in which the position of the object is out of a predetermined range.

A radiation detection device according to the invention comprises the radiography support device and the radiation detection panel.

A radiography apparatus according to the invention comprises the radiography support device; the radiation detection panel; and the radiation source.

According to the invention, there is provided a radiography support method that supports imaging of an object with a radiation detection panel in which a plurality of pixels are two-dimensionally arranged and which detects radiation emitted from a radiation source. The radiography support method comprises: a first reading control step of reading first pixel signals from at least some of the plurality of pixels in a state in which the radiation is not emitted from the radiation source and a state in which the object is placed on the radiation detection panel; an arithmetic step of calculating a position of the object with respect to the radiation detection panel on the basis of the first pixel signals; and a notification processing step of performing a notification process in a case in which the position of the object is out of a predetermined range.

According to the invention, there is provided a radiography support program that supports imaging of an object with a radiation detection panel in which a plurality of pixels are two-dimensionally arranged and which detects radiation emitted from a radiation source and causes a computer to perform: a first reading control step of reading first pixel signals from at least some of the plurality of pixels in a state in which the radiation is not emitted from the radiation source and a state in which the object is placed on the radiation detection panel; an arithmetic step of calculating a position of the object with respect to the radiation detection panel on the basis of the first pixel signals; and a notification processing step of performing a notification process in a case in which the position of the object is out of a predetermined range.

According to the invention, it is possible to provide a radiography support device that can calculate the position of an object with respect to a radiation detection panel, without adding a dedicated sensor to a radiation detection device, a radiation detection device comprising the radiography support device, a radiography apparatus comprising the radiography support device, a radiography support method, and a radiography support program.

DESCRIPTION OF THE PREFERRED EMBODIMENTS

Hereinafter, an embodiment of the invention will be described with reference to the drawings.

Figure 1:
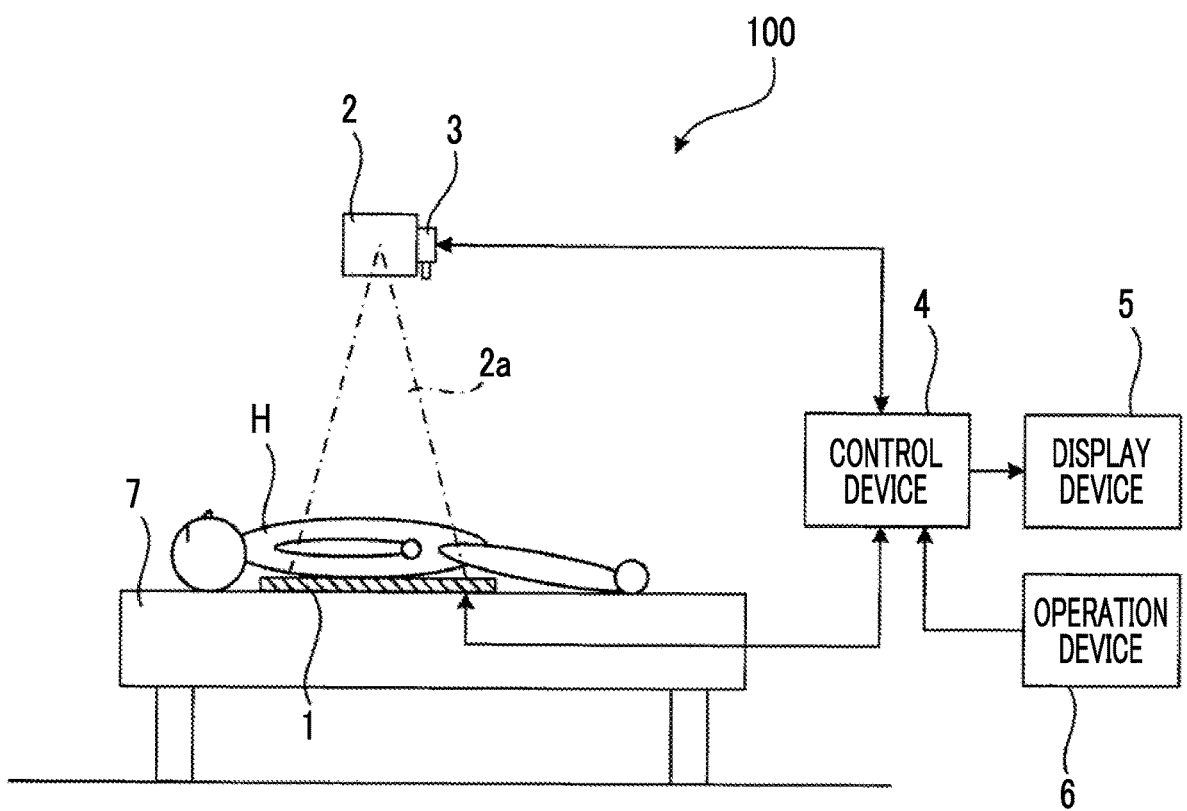
FIG. 1 is a diagram schematically illustrating the configuration of a radiography apparatus 100 which is an example of a radiography apparatus according to the invention.

FIG. 1 is a diagram schematically illustrating the configuration of a radiography apparatus 100.

The radiography apparatus 100 comprises an electronic cassette 1 forming a radiation detection device, a radiation source 2, an imaging device 3, a control device 4 that controls the overall operation of the radiography apparatus 100, a display device 5, and an operation device 6.

The radiation source 2 includes a radiation tube (not illustrated) that emits radiation (for example, X-rays) and an irradiation field limiter (not illustrated) that limits the irradiation field 2a of the radiation tube. The radiation source 2 is configured so as to be movable along a surface of an examination table 7 on which the electronic cassette 1 is placed.

The imaging device 3 is fixed to, for example, the radiation source 2. The imaging device 3 captures the irradiation field 2a of the radiation source 2 and transmits captured image data obtained by imaging to the control device 4 in response to a command from the control device 4.

The display device 5 is connected to the control device 4 such that it can communicate with the control device 4 in a wired manner or a wireless manner and displays various kinds of information transmitted from the control device 4.

The operation device 6 is an interface such as a keyboard, a mouse, or various buttons for inputting commands to the control device 4.

The control device 4 comprises various processors, a random access memory (RAM), and a read only memory (ROM).

The various processors include a central processing unit (CPU), a programmable logic device (PLD), and a dedicated electric circuit. The CPU is a general-purpose processor that executes a program to perform various processes. The PLD is a processor whose circuit configuration can be changed after it is manufactured, such as a field programmable gate array (FPGA). The dedicated electric circuit is a processor having a dedicated circuit configuration designed to perform a specific process, such as an application specific integrated circuit (ASIC).

Specifically, the structure of the various processors is an electric circuit (circuitry) which is a combination of circuit elements such as semiconductor elements.

The processor of the control device 4 may be one of the various processors or a combination of two or more processors of the same type or different types (for example, a combination of a plurality of FPGAs and a combination of a CPU and an FPGA).

The control device 4 is connected to the electronic cassette 1 such that it can communicate with the electronic cassette 1 in a wireless manner and controls the electronic cassette 1.

Specifically, the control device 4 transmits imaging conditions through the electronic cassette 1 and directs the electronic cassette 1 to set the signal processing conditions of a radiation detection panel 13 (see FIG. 2) which will be described below. In addition, the control device 4 transmits a synchronizing signal for synchronizing the emission time of radiation by the radiation source 2 with the exposure time of the radiation detection panel 13 to the electronic cassette 1 to control the synchronization of the radiation source 2 and the radiation detection panel 13.

The control device 4 receives image data output from the electronic cassette 1 and displays the image data on the display device 5, registers the image data in a server (not illustrated) in a hospital, or calculates the position of an object H with respect to the radiation detection panel 13 on the basis of the image data.

The control device 4 is connected to the imaging device 3 such that it can communicate with the imaging device 3 in a wired manner or a wireless manner and controls the imaging device 3. Specifically, the control device 4 transmits an imaging command to the imaging device 3 and acquires the captured image data in the irradiation field 2a from the imaging device 3.

Figure 2:
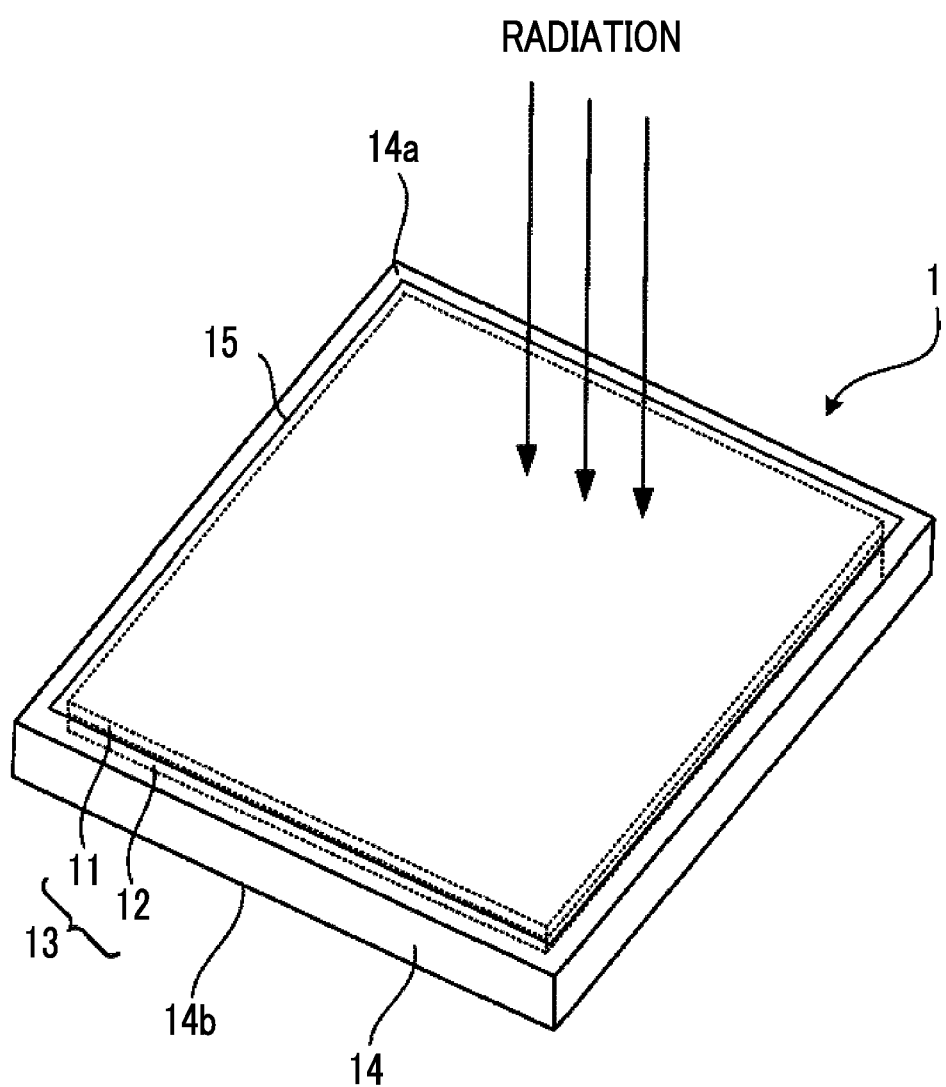
FIG. 2 is a diagram schematically illustrating the configuration of an electronic cassette 1 in the radiography apparatus 100 illustrated in FIG. 1.

FIG. 2 is a diagram schematically illustrating the configuration of the electronic cassette 1 in the radiography apparatus 100 illustrated in FIG. 1.

The electronic cassette 1 comprises a radiation detection panel 13 and a portable housing 14 that has a rectangular parallelepiped shape for accommodating the radiation detection panel 13.

A rectangular opening is formed in a front surface 14a of the housing 14. A transmission plate 15 that transmits radiation is attached to the opening.

The electronic cassette 1 is positioned in a posture in which a rear surface 14b of the housing 14 opposite to the front surface 14a comes into contact with the examination table 7 illustrated in FIG. 1 and the front surface 14a faces the radiation source 2. The electronic cassette 1 is irradiated with radiation from the upper side of the front surface 14a through an imaging target part of the object H that is a living body, such as a person, and is used.

The radiation detection panel 13 includes a scintillator 11 and a light detection substrate 12. The scintillator 11 and the light detection substrate 12 are sequentially stacked in the order of the scintillator 11 and the light detection substrate 12 as viewed from the front surface 14a on which radiation is incident.

The scintillator 11 has a phosphor, such as CsI:Tl (thallium-activated cesium iodide) or GOS ($Gd_2O_2S$:Tb, terbium-activated gadolinium oxysulfide), converts the radiation incident through the transmission plate 15 into visible light, and emits the visible light.

In addition, a radiation detection panel in which the light detection substrate 12 and the scintillator 11 are sequentially stacked as viewed from the front surface 14a on which radiation is incident may be used.

Furthermore, a direct-conversion-type radiation detection panel may be used which directly converts radiation into signal charge using a photoelectric conversion film such as an amorphous selenium film.

The light detection substrate 12 detects the visible light emitted from the scintillator 11 and converts the visible light into an image signal.

The housing 14 of the electronic cassette 1 accommodates, for example, a circuit substrate and a battery in addition to the above-mentioned components.

Figure 3:
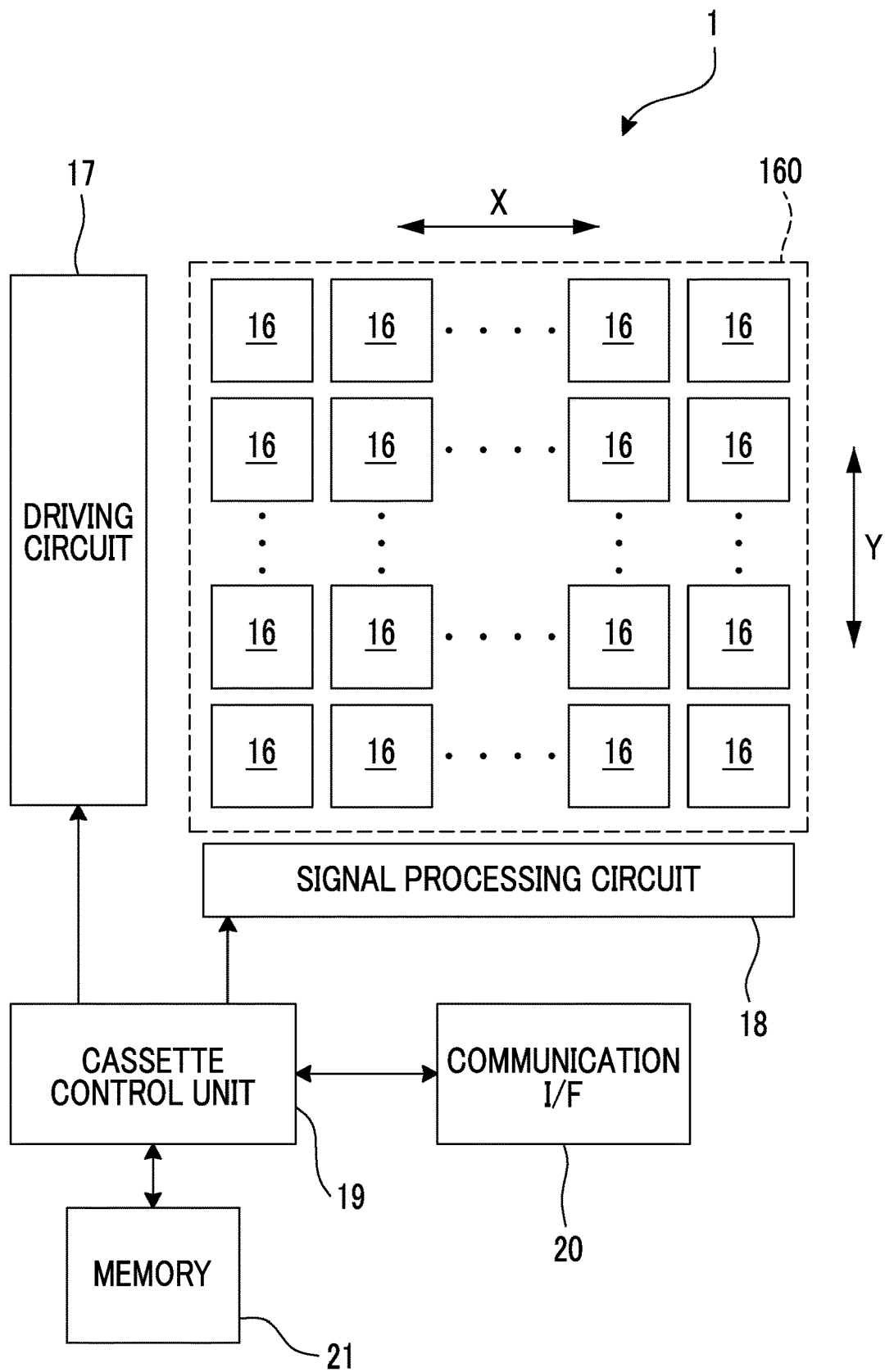
FIG. 3 is a diagram schematically illustrating the internal configuration of the electronic cassette 1 illustrated in FIG. 2.

FIG. 3 is a diagram schematically illustrating the internal configuration of the electronic cassette 1 illustrated in FIG. 2.

The electronic cassette 1 comprises an imaging region 160 which is a range of the light detection substrate 12 overlapping the transmission plate 15 illustrated in FIG. 2, a driving circuit 17 formed on the light detection substrate 12, a signal processing circuit 18 formed on the light detection substrate 12, a communication interface (I/F) 20 for wireless communication with the control device 4, a cassette control unit 19 controlling the driving circuit 17, the signal processing circuit 18, and the communication interface 20, and a memory 21 including a random access memory (RAM) and a read only memory (ROM).

A plurality of pixels 16 are two-dimensionally arranged in the imaging region 160. Specifically, a plurality of rows, each of which includes a plurality of pixels 16 arranged in a row direction X, are arranged in a column direction Y perpendicular to the row direction X in the imaging region 160.

The pixel 16 includes a photoelectric conversion unit that converts the visible light (radiation transmitted through the object H in the case of the direct-conversion-type radiation detection panel) emitted from the scintillator 11 into signal charge, a charge accumulation unit that accumulates the signal charge converted by the photoelectric conversion unit, and a transistor that converts the signal charge accumulated in the charge accumulation unit into a voltage signal (hereinafter, referred to as a pixel signal) and reads the voltage signal out to a signal line.

The driving circuit 17 drives, for example, the transistor of the pixel 16 and the photoelectric conversion unit of the pixel 16 in response to a command from the cassette control unit 19.

The signal processing circuit 18 performs signal processing, such as a digital conversion process, for the pixel signal, which has been read out to the signal line from each pixel 16 in the pixel row, under the conditions designated by the cassette control unit 19 and outputs the processed pixel signal. The pixel signal output from the signal processing circuit 18 is temporarily stored in the memory 21.

The cassette control unit 19 is formed by various processors which will be described below.

The cassette control unit 19 may be one of the various processors or a combination of two or more processors of the same type or different types (for example, a combination of a plurality of FPGAs or a combination of a CPU and an FPGA).

The cassette control unit 19 controls the driving circuit 17 and the signal processing circuit 18 in response to a command received from the control device 4 through the communication interface 20.

The cassette control unit 19, the communication interface 20, and the memory 21 are fixed to, for example, a supporting member (not illustrated) of the radiation detection panel 13 provided in the housing 14.

Figure 4:
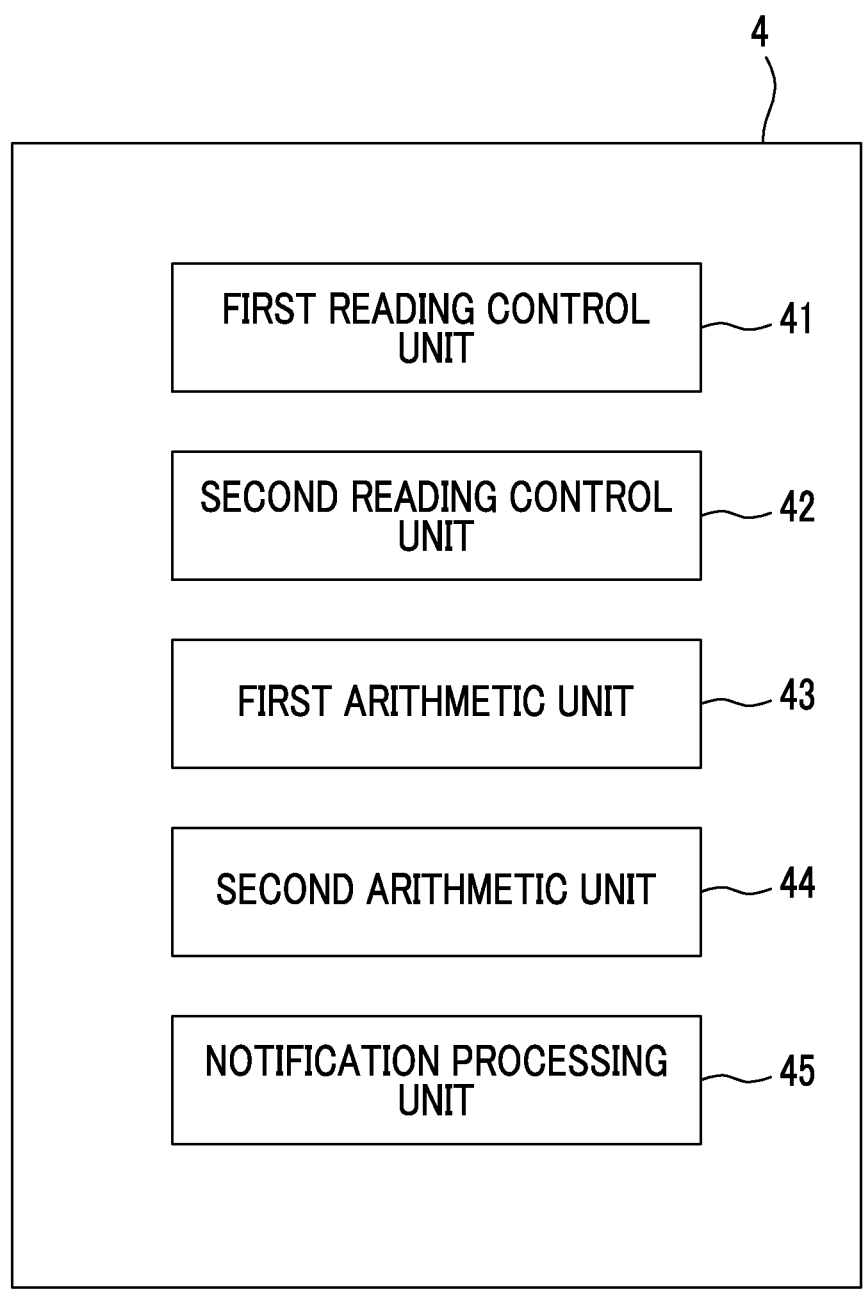
FIG. 4 is a diagram illustrating the functional blocks of a control device 4 in the radiography apparatus 100 illustrated in FIG. 1.

FIG. 4 is a diagram illustrating the functional blocks of the control device 4 in the radiography apparatus 100 illustrated in FIG. 1.

The processor of the control device 4 executes a radiography support program stored in the ROM provided in the control device 4 to function as a radiography support device comprising a first reading control unit 41, a second reading control unit 42, a first arithmetic unit 43, a second arithmetic unit 44, and a notification processing unit 45. The first reading control unit 41 and the second reading control unit 42 may be configured as one functional block. Similarly, the first arithmetic unit 43 and the second arithmetic unit 44 may be configured as one functional block.

The second reading control unit 42 performs a control process of acquiring a pixel signal (referred to as a second pixel signal) corresponding to the signal charge accumulated in the charge accumulation unit of each pixel 16 in a state in which each pixel 16 of the radiation detection panel 13 is not irradiated with radiation and a state in which the object H is not placed on the transmission plate 15 of the electronic cassette 1 (hereinafter, referred to as a no-load state). In this embodiment, the second pixel signal is acquired from all of the pixels 16 in the imaging region 160. However, the second pixel signal may be acquired from some of the pixels 16.

Specifically, the second reading control unit 42 transmits a command to acquire the second pixel signal to the electronic cassette 1 at the time when communication with the electronic cassette 1 is established.

The cassette control unit 19 of the electronic cassette 1 that has received the command controls the driving circuit 17 such that a pixel signal is read from each pixel 16. Then, the cassette control unit 19 calculates a variation (for example, dispersion) in the read pixel signal and determines whether the variation is equal to a design value.

In a case in which the variation is equal to the design value, the cassette control unit 19 treats the read pixel signal as the second pixel signal and transmits image data (hereinafter, referred to as no-load image data) which is a set of the second pixel signal to the control device 4.

In a case in which the variation is significantly different from the design value, the cassette control unit 19 performs a control process of reading a pixel signal from each pixel 16 again after a predetermined period of time and repeats the control process until the variation is equal to the design value.

The first reading control unit 41 performs a control process of acquiring a pixel signal (referred to as a first pixel signal) corresponding to the signal charge accumulated in the charge accumulation unit of each pixel 16 in a state in which each pixel 16 of the radiation detection panel 13 is not irradiated with radiation and a state in which the object H is placed on the transmission plate 15 of the electronic cassette 1 (hereinafter, referred to as a loaded state).

Specifically, in a case in which an operation (for example, the pressure of an imaging preparation completion button) indicating the completion of preparation for imaging is performed through the operation device 6, the first reading control unit 41 transmits a command to acquire the first pixel signal to the electronic cassette 1. It is assumed that the operation indicating the completion of preparation for imaging is performed in a state in which an imaging target part of the object H is positioned on the electronic cassette 1 placed on the examination table 7.

The first reading control unit 41 may determine a state in which the object H is placed on the electronic cassette 1 from the image captured by the imaging device 3 or whether there is a large difference between a variation in the pixel signal read from the pixel 16 and the design value.

The cassette control unit 19 of the electronic cassette 1 that has received the command controls the driving circuit 17 such that a pixel signal is read from each pixel 16. The cassette control unit 19 uses the read pixel signal as the first pixel signal and transmits image data (hereinafter, referred to as load image data) which is a set of the first pixel signals to the control device 4. In this embodiment, the first pixel signal is acquired from all of the pixels 16 in the imaging region 160. However, the first pixel signal may be acquired from some of the pixels 16.

The first arithmetic unit 43 calculates the position of the object H with respect to the radiation detection panel 13 on the basis of the load image data received from the electronic cassette 1.

Even in a state in which the imaging region 160 is not irradiated with radiation, signal charge is generated and accumulated in the charge accumulation unit of each pixel 16 of the radiation detection panel 13 illustrated in FIG. 3. The amount of signal charge increases as the load is applied to the pixel 16.

Figure 5:
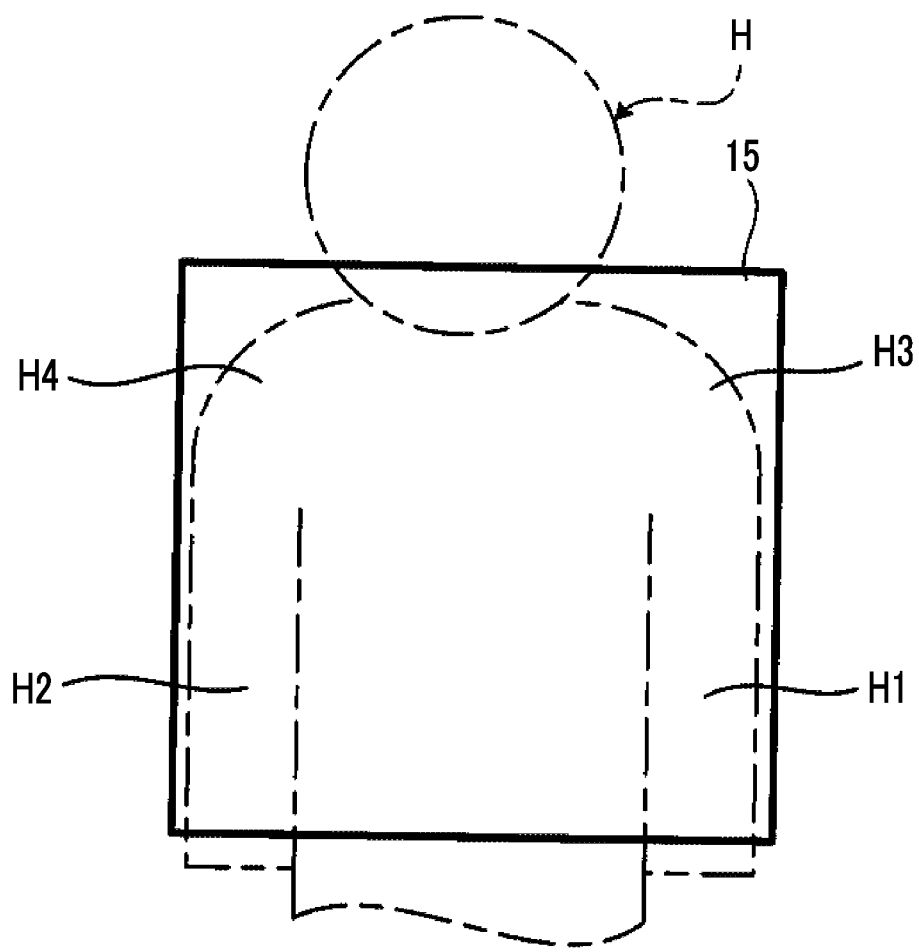
FIG. 5 is a diagram schematically illustrating an example of a state in which an object H lies face up on a transmission plate 15 of the electronic cassette 1.

FIG. 5 is a diagram schematically illustrating an example of the state in which the object H lies face up on the transmission plate 15 of the electronic cassette 1. FIG. 5 illustrates a case in which the chest of the object H is the imaging target part. In the example illustrated in FIG. 5, the left elbow H1, right elbow H2, left shoulder H3, and right shoulder H4 of the object H particularly apply a load to the transmission plate 15.

Figure 6:
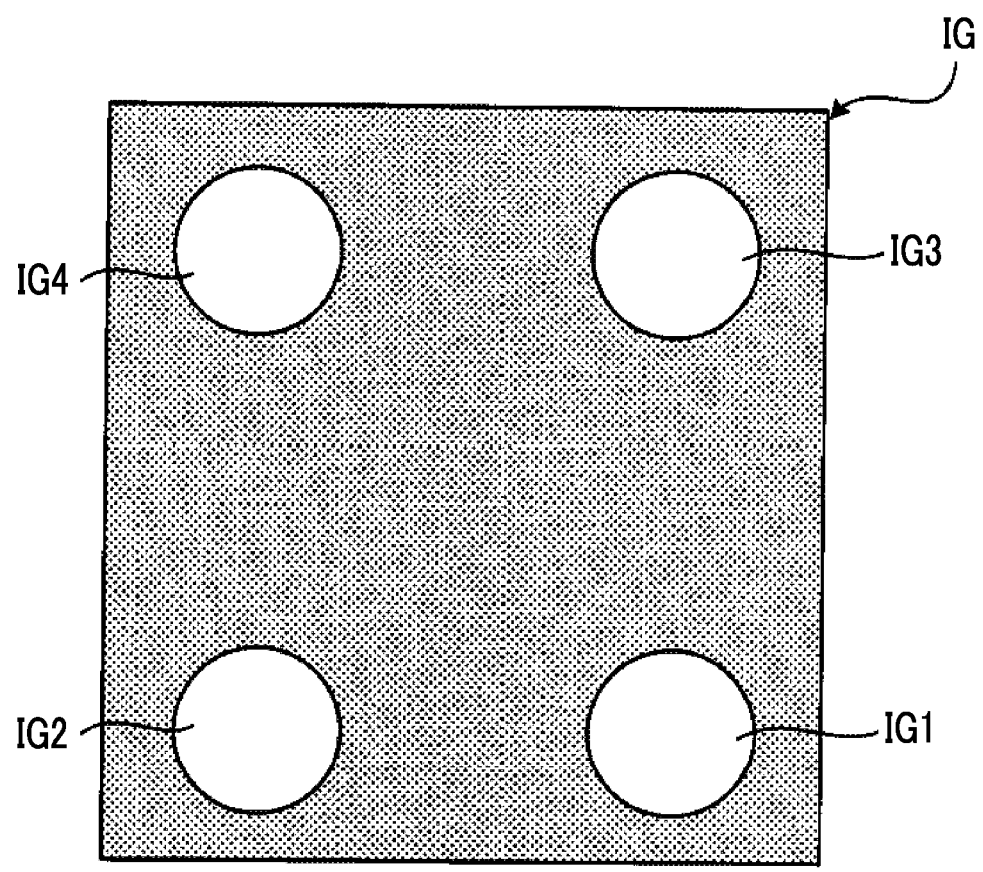
FIG. 6 is a diagram illustrating an image based on pixel signals read from each pixel 16 of a radiation detection panel 13 in the state illustrated in FIG. 5 and a state in which radiation is not emitted.

FIG. 6 is a diagram illustrating an image based on the pixel signals read from each pixel 16 of the radiation detection panel 13 in the state illustrated in FIG. 5 or the state in which no radiation is emitted.

In an image IG illustrated in FIG. 6, the signal levels of a region IG1 corresponding to the left elbow H1 of the object H, a region IG2 corresponding to the right elbow H2, a region IG3 corresponding to the left shoulder H3, and a region IG4 corresponding to the right shoulder H4 are higher than the signal levels of the other regions (a region hatched with dots).

As such, the radiation detection panel 13 has the characteristic that the levels of the pixel signals read from the pixels 16 in a portion of the imaging region 160 to which a large load is applied are high as illustrated in FIG. 6. The first arithmetic unit 43 calculates the position of the object H on the radiation detection panel 13 using this characteristic. Hereinafter, a method for calculating the position will be described.

First, the first arithmetic unit 43 acquires the no-load image data obtained by the control of the second reading control unit 42. Then, the first arithmetic unit 43 calculates the average value of the second pixel signals forming the no-load image data as an offset value of the pixel signals read from each pixel 16 of the radiation detection panel 13 and stores the average value in the RAM.

In addition, the first arithmetic unit 43 may divide the no-load image data into a plurality of regions, calculate the average value of the second pixel signals belonging to each divided region, and store the average value as the offset value of each pixel 16 corresponding to the divided region. Alternatively, the first arithmetic unit 43 may store each second pixel signal forming the no-load image data as the offset value of each pixel 16 from which the second pixel signal has been read.

Then, the first arithmetic unit 43 acquires the load image data obtained by the control of the first reading control unit 41. Then, the first arithmetic unit 43 subtracts the offset value corresponding to each pixel 16, from which the first pixel signal has been read, from each of the first pixel signals forming the load image data.

Then, the first arithmetic unit 43 specifies the pixel 16, from which a first pixel signal having a level equal to or greater than a predetermined threshold value among the first pixel signals after the subtraction of the offset value has been read, as a loaded pixel that is subjected to the load from the object H.

Figure 7:
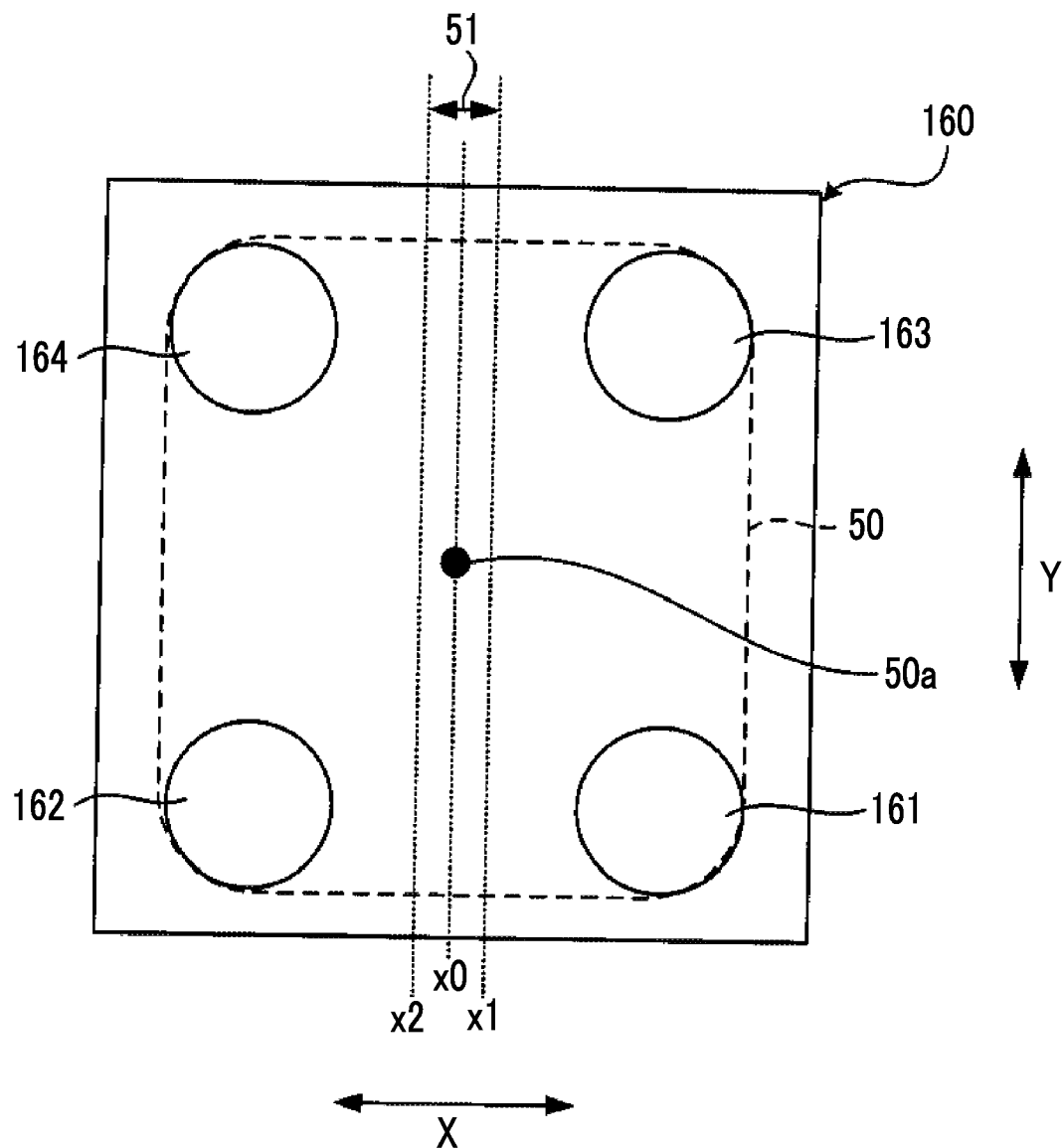
FIG. 7 is a diagram schematically illustrating an example of the arrangement of loaded pixels specified in the state illustrated in FIG. 5.

FIG. 7 is a diagram schematically illustrating an example of the arrangement of the loaded pixels specified in the state illustrated in FIG. 5.

As illustrated in FIG. 7, the imaging region 160 includes a region 161 including the loaded pixels subjected to the load from the left elbow H1, a region 162 including the loaded pixels subjected to the load from the right elbow H2, a region 163 including the loaded pixels subjected to the load from the left shoulder H3, and a region 164 including the loaded pixels subjected to the load from the right shoulder H4.

The first arithmetic unit 43 calculates a gravity center position 50*a* of a range 50 surrounded by the region 161, the region 162, the region 163, and the region 164 illustrated in FIG. 7 in the imaging region 160 and calculates the gravity center position 50*a* as the position of the object H with respect to the radiation detection panel 13.

The range 50 surrounded by the region 161, the region 162, the region 163, and the region 164 is obtained by, for example, calculating the gravity center positions of the region 161, the region 162, the region 163, and the region 164 and connecting the four gravity center positions.

In addition, the range 50 may be determined by extracting the pixels 16 that are farthest from or closest to the center of the imaging region 160 from each of the region 161, the region 162, the region 163, and the region 164 and connecting the four extracted pixels 16.

The gravity center of the range 50 may be calculated by calculating the area of each of the region 161, the region 162, the region 163, and the region 164 and performing weighting such that the gravity center position is close to the region with a large area.

The position of the radiation detection panel 13 is defined as, for example, the center position of the imaging region 160. Therefore, the gravity center position 50a in the imaging region 160 can be calculated by the above-mentioned method to calculate the position of the object H with respect to the radiation detection panel 13.

Returning to the description of the FIG. 4, the second arithmetic unit 44 calculates the position of the object H with respect to the radiation source 2.

Specifically, in a case in which an operation indicating the completion of preparation for imaging is performed, the second arithmetic unit 44 transmits an imaging start command to the imaging device 3. The imaging device 3 that has received the command captures the image of the object H overlapping the irradiation field 2a and transmits the captured image data to the control device 4.

The second arithmetic unit 44 acquires the captured image data and calculates the center position of the imaging target part (for example, the chest) of the object H included in the captured image data as the position of the object H with respect to the radiation source 2.

The coordinates of a region corresponding to the irradiation field 2a in the captured image data have been known and the center of the region is defined as the position of the radiation source 2. Therefore, the center position of the imaging target part can be calculated as the position of the object H with respect to the radiation source 2.

The notification processing unit 45 illustrated in FIG. 4 determines whether the position (the gravity center position 50a illustrated in FIG. 7) of the object H calculated by the first arithmetic unit 43 is out of a range 51 that is predetermined with respect to the imaging region 160. In a case in which the position of the object H is out of the range 51, the notification processing unit 45 performs a first notification process.

The range 51 illustrated in FIG. 7 is set as a range from a center position x0 of the imaging region 160 in a row direction X to positions x1 and x2 that are a predetermined distance away from the center position x0 in one direction of the row direction X and the other direction of the row direction X, respectively.

Specifically, the first notification process outputs information for displaying a message indicating that there is a relative positional deviation between the electronic cassette 1 and the object H to the display device 5 such that the message is displayed by the display device 5.

The first notification process may output the information for outputting the message indicating that there is a relative positional deviation between the electronic cassette 1 and the object H to a speaker (not illustrated) such that the message is output as a voice.

The notification processing unit 45 determines whether the position of the object H calculated by the second arithmetic unit 44 is out of a predetermined range having, as its center, the center of a region corresponding to the irradiation field 2a in the captured image data. In a case in which the position of the object H is out of the range, the notification processing unit 45 performs a second notification process.

Specifically, the second notification process outputs information for displaying a message indicating that there is a relative positional deviation between the radiation source 2 and the object H to the display device 5 such that the message is displayed by the display device 5.

The second notification process may output the information for outputting the message indicating that there is a relative positional deviation between the radiation source 2 and the object H to the speaker (not illustrated) such that the message is output as a voice.

Figure 8:
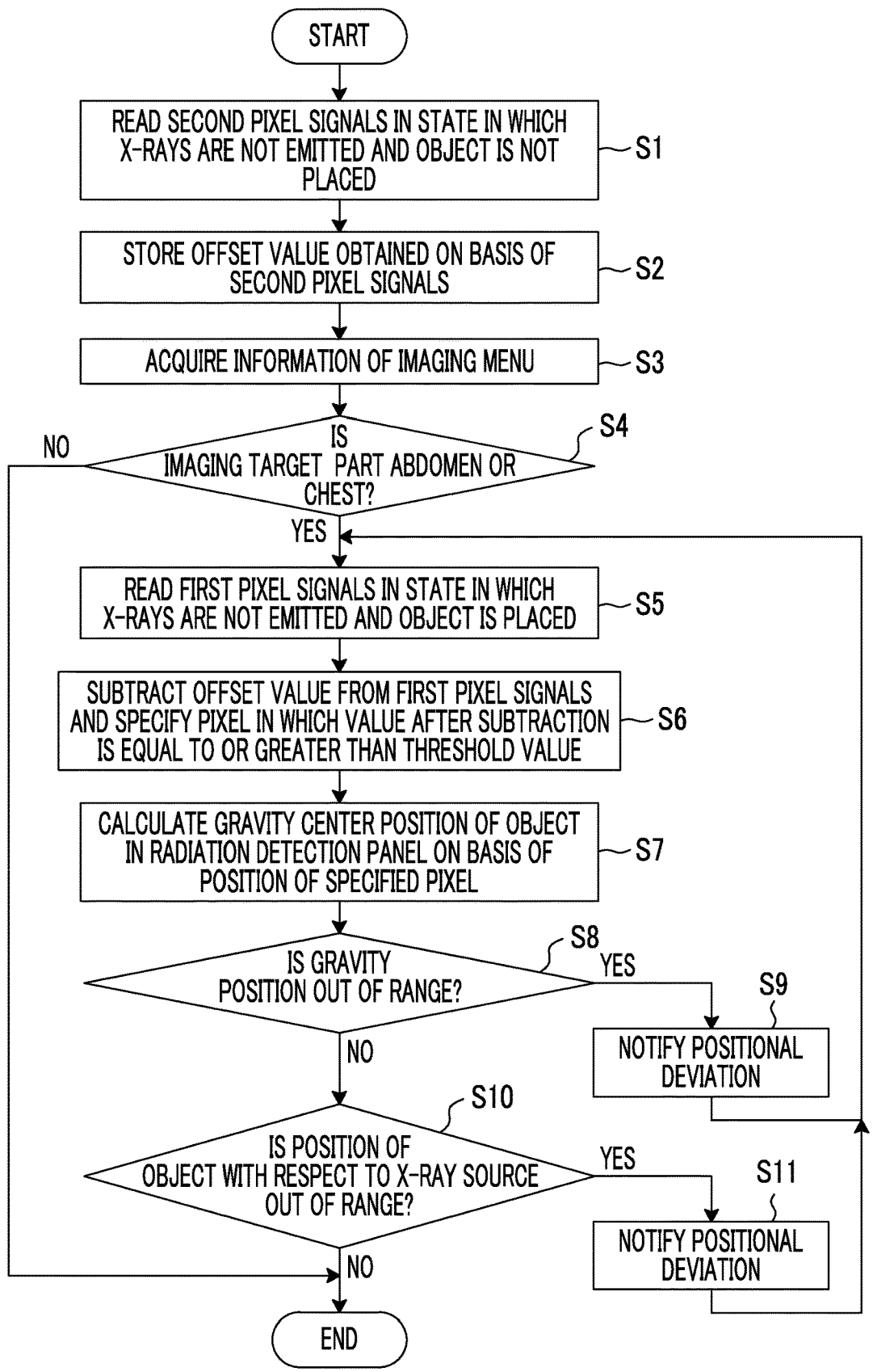
FIG. 8 is a flowchart illustrating the operation of the control device 4 in the radiography apparatus 100 illustrated in FIG. 1.

FIG. 8 is a flowchart illustrating the operation of the control device 4 in the radiography apparatus 100 illustrated in FIG. 1.

First, a technician places the electronic cassette 1 on the examination table 7. Then, in a case in which communication with the electronic cassette 1 is established, the second reading control unit 42 of the control device 4 transmits a command to read the second pixel signal to the electronic cassette 1. Then, the second pixel signal is read from each pixel 16 of the electronic cassette 1 (Step S1). Then, the control device 4 acquires the second pixel signals.

In a case in which the second pixel signals are acquired, the first arithmetic unit 43 of the control device 4 calculates the offset value on the basis of the second pixel signals and stores the offset value in the RAM (Step S2).

The technician operates the operation device 6 to input information indicating imaging conditions and the imaging target part, positions the electronic cassette 1, the object H, and the radiation source 2, and presses the imaging preparation completion button.

In a case in which the imaging preparation completion button is pressed, the control device 4 acquires the information of the imaging target part set by the technician (Step S3) and determines whether the imaging target part is the chest or the abdomen (Step S4).

In a case in which the imaging target part is, for example, a hand or a leg and is not the chest or the abdomen (Step S4: NO), the control device 4 changes to an imaging standby state.

In a case in which an operation for starting the emission of radiation is performed in the imaging standby state, the emission of radiation and the exposure of each pixel 16 of the electronic cassette 1 are performed in synchronization with each other and radiography is performed.

In a case in which the imaging target part is the chest or the abdomen (Step S4: YES), the first reading control unit 41 of the control device 4 transmits a command to read the first pixel signal to the electronic cassette 1. Then, the first pixel signal is read from each pixel 16 of the electronic cassette 1 (Step S5). Then, the control device 4 acquires the first pixel signals.

In a case in which the first pixel signals are acquired, the first arithmetic unit 43 of the control device 4 subtracts the offset value stored in the RAM in Step S2 from the first pixel signals and specifies the loaded pixels on the basis of the first pixel signals after the subtraction (Step S6).

Then, the first arithmetic unit 43 of the control device 4 calculates the position (the gravity center position 50a in FIG. 7) of the object H in the imaging region 160 on the basis of the position of the specified loaded pixels (Step S7).

Then, the notification processing unit 45 of the control device 4 determines whether the position of the object H calculated in Step S7 is out of the range that is predetermined with respect to the imaging region 160 (Step S8).

In a case in which the determination result in Step S8 is "YES", the notification processing unit 45 of the control device 4 displays a message indicating the deviation of the object H from the electronic cassette 1 on the display device 5 to notify the technician of the deviation of the position (Step S9).

After Step S9, the technician adjusts the position of at least one of the electronic cassette 1 or the object H. In a case in which the technician presses an adjustment completion button included in the operation device 6, the process returns to Step S5.

In a case in which the determination result in Step S8 is "NO", the second arithmetic unit 44 of the control device 4 controls the imaging device 3 such that captured image data is acquired from the imaging device 3 and calculates the position of the object H with respect to the radiation source 2 on the basis of the captured image data.

Then, the notification processing unit 45 of the control device 4 determines whether the position of the object H calculated by the second arithmetic unit 44 is out of the range that is predetermined with respect to the region corresponding to the irradiation field 2a in the captured image data (Step S10).

In a case in which the determination result in Step S10 is "YES", the notification processing unit 45 of control device 4 displays a message indicating the deviation of the radiation source 2 from the object H on the display device 5 to notify the technician of the positional deviation (Step S11).

After Step S11, the technician adjusts the position of at least one of the radiation source 2 or the object H. In a case in which the technician presses the adjustment completion button, the process returns to Step S5.

As such, in a case in which the adjustment of the position is repeated and the determination result in Step S10 is "NO", the control device 4 changes to the imaging standby state. In a case in which the determination result in Step S10 is "NO", the exposure of the radiation source 2 may be unlocked and a message indicating that imaging is available may be displayed on the display device 5.

As described above, according to the radiography apparatus 100, the position of the object H with respect o the radiation detection panel 13 is calculated on the basis of the pixel signals obtained from the radiation detection panel 13. Therefore, it is not necessary to provide a dedicated sensor in the electronic cassette 1 and to reduce manufacturing costs. In addition, since it is not necessary to provide a dedicated sensor in the radiation detection panel 13, it is possible to improve the quality of a captured image.

In addition, according to the radiography apparatus 100, only in a case in which the imaging target part is the chest or the abdomen, the functions of the first reading control unit 41, the first arithmetic unit 43, the second arithmetic unit 44, and the notification processing unit 45 are activated.

In a case in which the imaging target part is the chest or the abdomen, the transmission plate 15 is likely to be hidden by the object H. Therefore, the functions of the first reading control unit 41, the first arithmetic unit 43, and the notification processing unit 45 can effectively prevent a failure in imaging.

In contrast, in a case in which the imaging target part is, for example, a hand or a leg, the transmission plate 15 is unlikely to be hidden by the object H. Therefore, in this case, the control device immediately changes to the imaging standby state, which makes it possible to improve examination efficiency. In addition, in this case, since the reading of the first pixel signals is not performed, it is possible to prevent a reduction in the remaining battery level of the electronic cassette 1.

In addition, the functions of the first reading control unit 41, the first arithmetic unit 43, the second arithmetic unit 44, and the notification processing unit 45 may be always activated regardless of the imaging target part. That is, Step S4 may be removed in FIG. 8 and the process may proceed to Step S5 after Step S3.

In this case, preferably, the range set in the imaging region 160 which is compared with the gravity center position of the object in Step S8 is changed depending on the imaging target part.

For example, in the case of a living body part such as a hand or a leg, the range is expanded. In the case of a large living body part such as the chest or the abdomen, the range may be narrowed.

The transmission plate 15 is unlikely to be hidden by the small living body part and there is little limitation in the arrangement position of the small living body part on the transmission plate 15. Therefore, in a case in which the range is expanded, the probability that the determination result in Step S8 will be "YES" is reduced and it is possible to increase examination efficiency. In contrast, for the small living body part, in a case in which the range is narrowed, it is possible to prevent the imaging target part from largely protruding outward from the transmission plate 15 and thus to prevent a failure in imaging.

Next, another example of the method for calculating the position of the object H with respect to the radiation detection panel 13 will be described.

Figure 9:
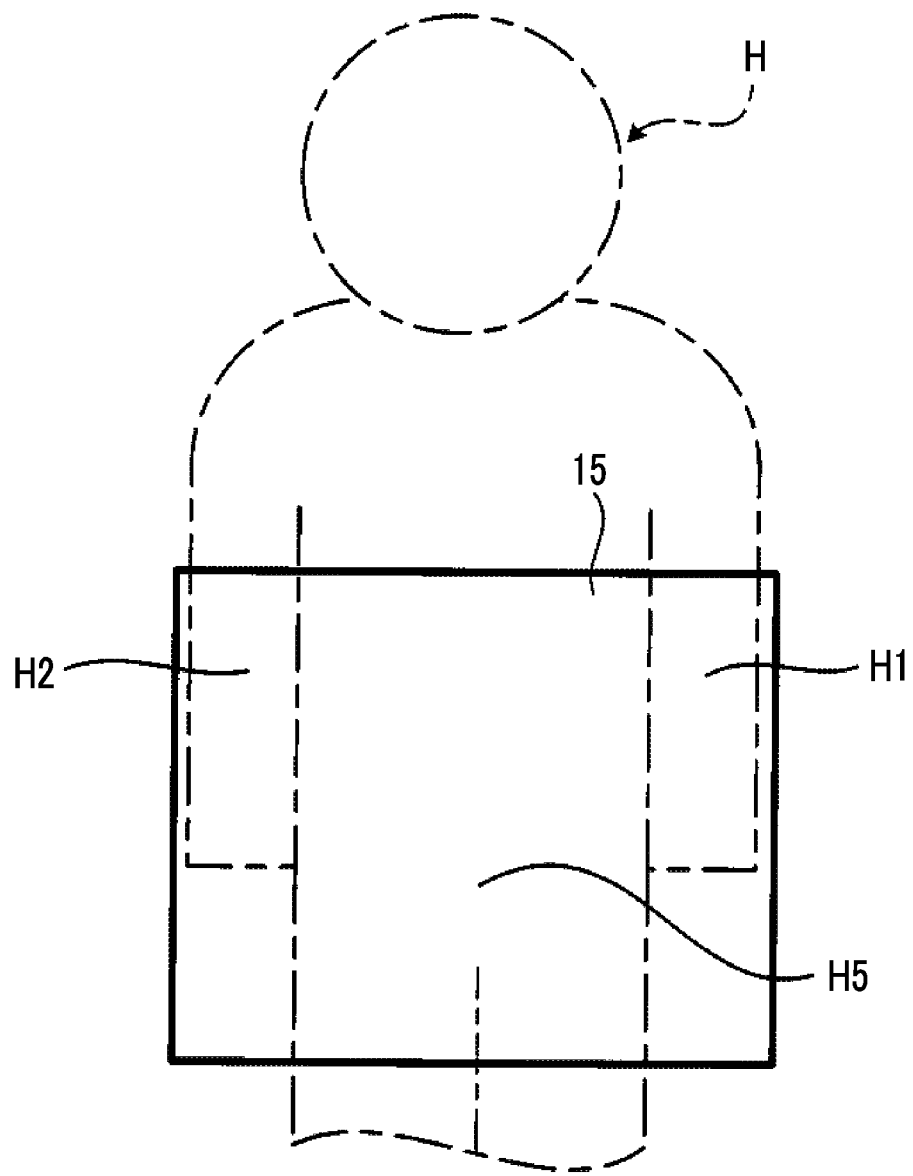
FIG. 9 is a diagram schematically illustrating another example of the state in which the object H lies face up on the transmission plate 15 of the electronic cassette 1.

FIG. 9 is a diagram schematically illustrating another example of the state in which the object H lies face up on the transmission plate 15 of the electronic cassette 1. FIG. 9 illustrates a case in which the imaging target part is the abdomen of the object H. In the example illustrated in FIG. 9, particularly, the left elbow H1, right elbow H2, and waist H5 of the object H apply a load to the transmission plate 15.

Figure 10:
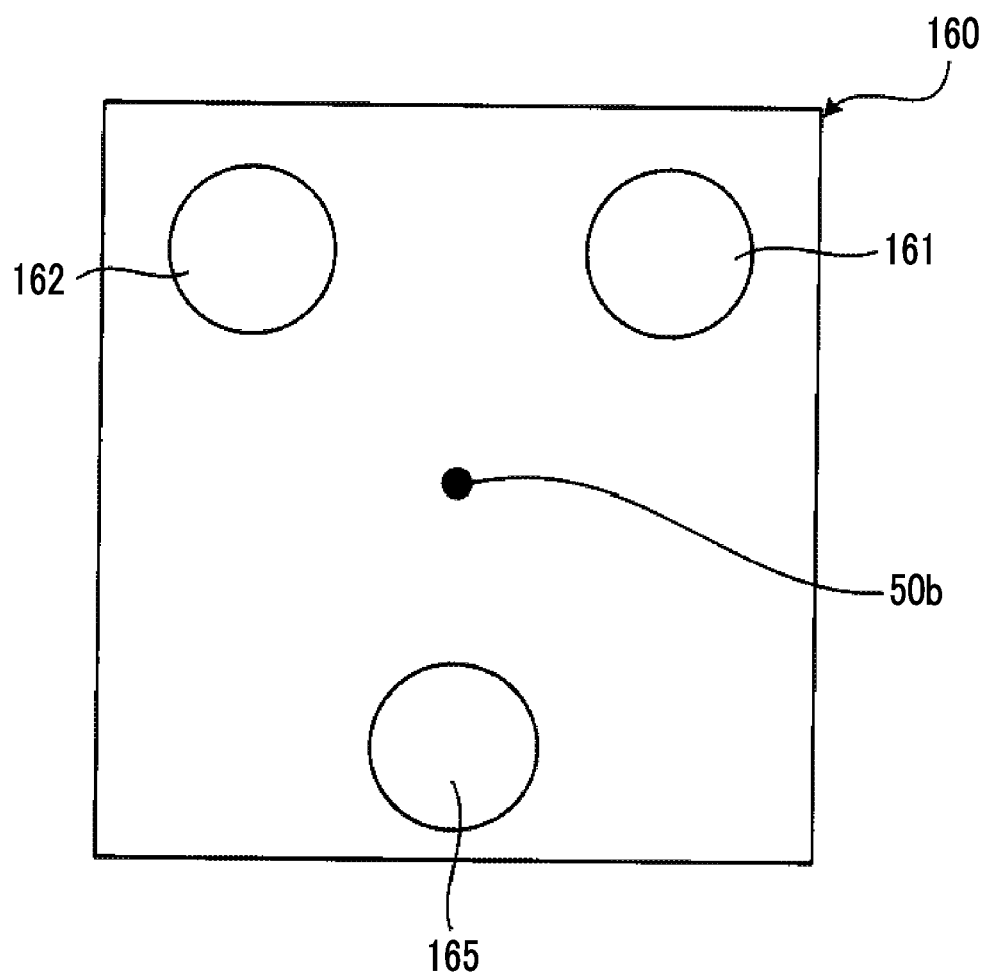
FIG. 10 is a diagram schematically illustrating an example of the arrangement of the loaded pixels specified in the state illustrated in FIG. 9.

FIG. 10 is a diagram schematically illustrating an example of the arrangement of the loaded pixels specified in the state illustrated in FIG. 9.

As illustrated in FIG. 10, the imaging region 160 includes a region 161 including the loaded pixels subjected to the load from the left elbow H1, a region 162 including the loaded pixels subjected to the load from the right elbow H2, and a region 165 including the loaded pixels subjected to the load from the waist H5.

The first arithmetic unit 43 calculates a gravity center position 50b of a range that is surrounded by the region 161, the region 162, and the region 165 illustrated in FIG. 10 in the imaging region 160 and calculates the gravity center position 50b as the position of the object H with respect to the radiation detection panel 13.

In a case in which there are three or more regions including the loaded pixels as illustrated in FIGS. 7 and 10, the gravity center position of a region surrounded by the three or more regions is used as the position of the object H. This configuration makes it possible to calculate the position of the object H with respect to the radiation detection panel 13 with high accuracy.

Figure 11:
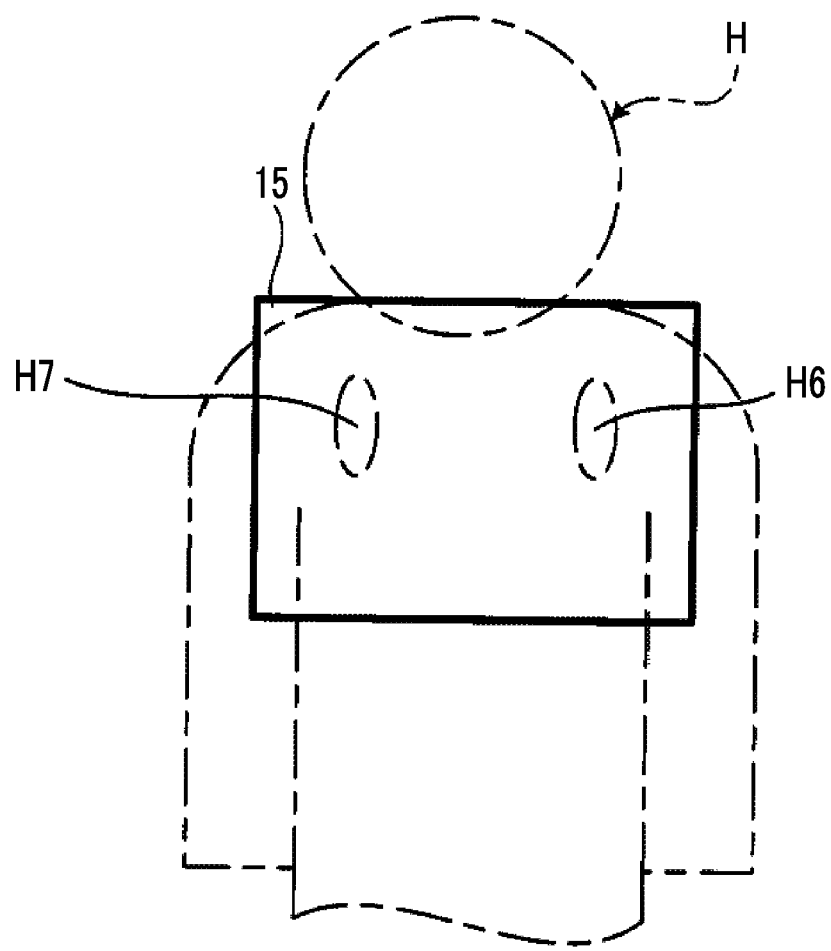
FIG. 11 is a diagram schematically illustrating still another example of the state in which the object H lies face up on the transmission plate 15 of the electronic cassette 1.

FIG. 11 is a diagram schematically illustrating still another example of the state in which the object H lies face up on the transmission plate 15 of the electronic cassette 1. FIG. 11 illustrates a case in which the imaging target part is the back of the object H. In the example illustrated in FIG. 11, particularly, the left and right scapulae H6 and H7 of the object H apply a load to the transmission plate 15.

Figure 12:
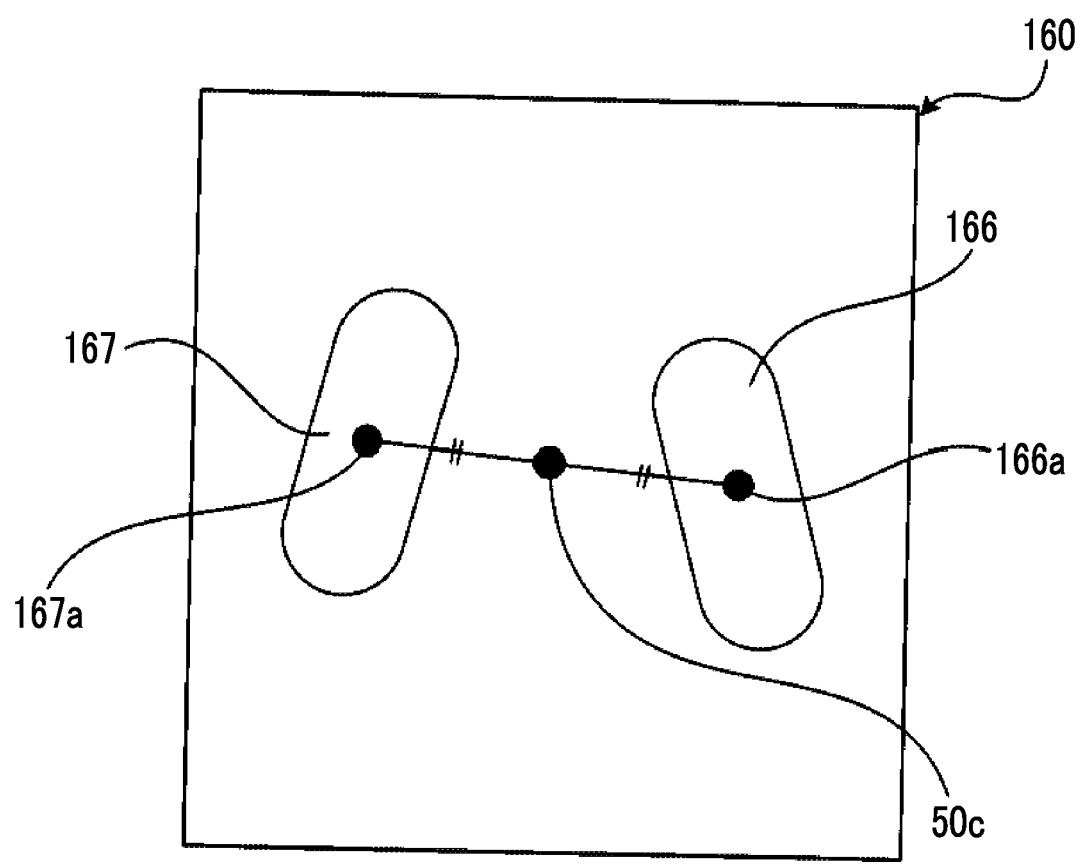
FIG. 12 is a diagram schematically illustrating an example of the arrangement of the loaded pixels specified in the state illustrated in FIG. 11.

FIG. 12 is a diagram schematically illustrating an example of the arrangement of the loaded pixels specified in the state illustrated in FIG. 11.

As illustrated in FIG. 12, the imaging region 160 includes a region 166 including the loaded pixels subjected to the load from the left scapula H6 and a region 167 including the loaded pixels subjected to the load from the right scapula H7.

The first arithmetic unit 43 calculates an intermediate position 50c between a gravity center position 166a of the region 166 and a gravity center position 167a of the region 167 illustrated in FIG. 12 in the imaging region 160 and calculates the intermediate position 50c as the position of the object H with respect to the radiation detection panel 13.

In a case in which there are two regions including the loaded pixels as illustrated in FIG. 12, the intermediate position between the gravity centers of the two regions is used as the position of the object H. This configuration makes it possible to calculate the position of the object H with respect to the radiation detection panel 13 with high accuracy.

In the radiography apparatus 100 that has been described so far, the cassette control unit 19 of the electronic cassette 1 may have the functional blocks of the control device 4 illustrated in FIG. 4. In this case, the cassette control unit 19 functions as the radiography support device.

In addition, the second arithmetic unit 44 of the control device 4 is not essential and may be omitted.

As described above, the specification discloses the following.

(1) There is provided a radiography support device that supports imaging of an object with a radiation detection panel in which a plurality of pixels are two-dimensionally arranged and which detects radiation emitted from a radiation source. The radiography support device comprises: a first reading control unit that reads first pixel signals from at least some of the plurality of pixels in a state in which the radiation is not emitted from the radiation source and a state in which the object is placed on the radiation detection panel; a first arithmetic unit that calculates a position of the object with respect to the radiation detection panel on the basis of the first pixel signals; and a notification processing unit that performs a notification process in a case in which the position of the object is out of a predetermined range.

(2) The radiography support device according to (1) further comprises a second reading control unit that reads second pixel signals from at least some of the plurality of pixels in the state in which the radiation is not emitted from the radiation source and a state in which the object is not placed on the radiation detection panel. The first arithmetic unit specifies a pixel of which a value obtained by processing the first pixel signal using a value obtained on the basis of the second pixel signals is equal to or greater than a threshold value and calculates the position of the object with respect to the radiation detection panel on the basis of a position of the specified pixel.

(3) In the radiography support device according to (2), in a case in which there are three or more regions including the specified pixel, the first arithmetic unit calculates a gravity center position of a range surrounded by the three or more regions as the position of the object.

(4) In the radiography support device according to (2) or (3), in a case in which there are two regions including the specified pixel, the first arithmetic unit calculates an intermediate position between the gravity centers of the two regions as the position of the object.

(5) In the radiography support device according to any one of (1) to (4), in a case in which information for using a chest or an abdomen of a living body as the object is set in a radiography apparatus, functions of the first reading control unit, the first arithmetic unit, and the notification processing unit are activated.

(6) In the radiography support device according to any one of (1) to (4), the predetermined range changes depending on an imaging target part of the object.

(7) The radiography support device according to any one of (1) to (6) further comprises a second arithmetic unit that calculates a position of the object with respect to the radiation source. In a case in which the position calculated by the second arithmetic unit is out of a predetermined range, the notification processing unit performs a notification process.

(8) There is provided a radiation detection device comprising: the radiography support device according to any one of (1) to (7); and the radiation detection panel.

(9) There is provided a radiography apparatus comprising: the radiography support device according to any one of (1) to (7); the radiation detection panel; and the radiation source.

(10) In the radiography support device according to any one of (1) to (7), the radiography support device is provided in a control device that is provided outside a radiation detection device including the radiation detection panel and is communicable with the radiation detection device.

(11) There is provided a radiography support method that supports imaging of an object with a radiation detection panel in which a plurality of pixels are two-dimensionally arranged and which detects radiation emitted from a radiation source. The radiography support method comprises: a first reading control step of reading first pixel signals from at least some of the plurality of pixels in a state in which the radiation is not emitted from the radiation source and a state in which the object is placed on the radiation detection panel; an arithmetic step of calculating a position of the object with respect to the radiation detection panel on the basis of the first pixel signals; and a notification processing step of performing a notification process in a case in which the position of the object is out of a predetermined range.

(12) There is provided a radiography support program that supports imaging of an object with a radiation detection panel in which a plurality of pixels are two-dimensionally arranged and which detects radiation emitted from a radiation source and causes a computer to perform: a first reading control step of reading first pixel signals from at least some of the plurality of pixels in a state in which the radiation is not emitted from the radiation source and a state in which the object is placed on the radiation detection panel; an arithmetic step of calculating a position of the object with respect to the radiation detection panel on the basis of the first pixel signals; and a notification processing step of performing a notification process in a case in which the position of the object is out of a predetermined range.

According to the invention, it is possible to provide a radiography support device that can calculate the position of an object with respect to a radiation detection panel without adding a dedicated sensor to a radiation detection device, a radiation detection device comprising the radiography support device, a radiography support method, and a radiography support program.

EXPLANATION OF REFERENCES

100: radiography apparatus
1: electronic cassette
2: radiation source
2a: irradiation field
11: scintillator
12: light detection substrate
13: radiation detection panel
14: housing 14a: front surface
14b: rear surface
15: transmission plate
16: pixel
160: imaging region
17: driving circuit
18: signal processing circuit
19: cassette control unit
20: communication interface
21: memory
2: radiation source
3: imaging device
4: control device
41: first reading control unit
42: second reading control unit
43: first arithmetic unit
44: second arithmetic unit
45: notification processing unit
5: display device
6: operation device
7: examination table
IG: image
IG1, IG2, IG3, IG4: region
H: object
H1: left elbow
H2: right elbow
H3: left shoulder
H4: right shoulder
H5: waist
H6: left scapula
H7: right scapula
161, 162, 163, 164, 165, 166, 167: region including loaded pixels
50, 51: range
50a, 50b, 166a, 167a: gravity center position
50c: intermediate position

What is claimed is:

1. A radiography support device that supports imaging of an object with a radiation detection panel in which a plurality of pixels are two-dimensionally arranged and which detects radiation emitted from a radiation source, the device comprising:
a first reading control unit that reads first pixel signals from at least some of the plurality of pixels in a state in which the radiation is not emitted from the radiation source and a state in which the object is placed on the radiation detection panel;
a first arithmetic unit that calculates a position of the object with respect to the radiation detection panel based on the first pixel signals; and
a notification processing unit that performs a notification process in a case in which the position of the object is out of a predetermined range.

2. The radiography support device according to claim 1, further comprising:
a second reading control unit that reads second pixel signals from at least some of the plurality of pixels in the state in which the radiation is not emitted from the radiation source and a state in which the object is not placed on the radiation detection panel,
wherein the first arithmetic unit specifies a pixel of which a value obtained by processing the first pixel signal using a value obtained based on the second pixel signals is equal to or greater than a threshold value and calculates the position of the object with respect to the radiation detection panel based on a position of the specified pixel.

3. The radiography support device according to claim 2, wherein, in a case in which there are three or more separated regions including the specified pixel, the first arithmetic unit calculates a gravity center position of a range surrounded by the three or more separated regions as the position of the object.

4. The radiography support device according to claim 2, wherein, in a case in which there are two separated regions including the specified pixel, the first arithmetic unit calculates an intermediate position between gravity centers of the two separated regions as the position of the object.

5. The radiography support device according to claim 3, wherein, in a case in which there are two separated regions including the specified pixel, the first arithmetic unit calculates an intermediate position between gravity centers of the two separated regions as the position of the object.

6. The radiography support device according to claim 1, wherein, in a case in which information for using a chest or an abdomen of a living body as the object is set in a radiography apparatus, functions of the first reading control unit, the first arithmetic unit, and the notification processing unit are activated.

7. The radiography support device according to claim 2, wherein, in a case in which information for using a chest or an abdomen of a living body as the object is set in a radiography apparatus, functions of the first reading control unit, the first arithmetic unit, and the notification processing unit are activated.

8. The radiography support device according to claim 1, wherein the predetermined range changes depending on an imaging target part of the object.

9. The radiography support device according to claim 2, wherein the predetermined range changes depending on an imaging target part of the object.

10. The radiography support device according to claim 1, further comprising:
a second arithmetic unit that calculates a position of the object with respect to the radiation source,
wherein, in a case in which the position calculated by the second arithmetic unit is out of a predetermined range, the notification processing unit performs a notification process.

11. The radiography support device according to claim 2, further comprising:
a second arithmetic unit that calculates a position of the object with respect to the radiation source,
wherein, in a case in which the position calculated by the second arithmetic unit is out of a predetermined range, the notification processing unit performs a notification process.

12. A radiation detection device comprising:
the radiography support device according to claim 1; and
the radiation detection panel.

13. A radiography apparatus comprising:
the radiography support device according to claim 1;
the radiation detection panel; and
the radiation source.

14. The radiography support device according to claim 1, wherein the radiography support device is provided in a control device that is provided outside a radiation detection device including the radiation detection panel and is communicable with the radiation detection device.

15. The radiography support device according to claim 2, wherein the radiography support device is provided in a control device that is provided outside a radiation detection device including the radiation detection panel and is communicable with the radiation detection device.

16. A radiography support method that supports imaging of an object with a radiation detection panel in which a plurality of pixels are two-dimensionally arranged and which detects radiation emitted from a radiation source, the method comprising:
- a first reading control step of reading first pixel signals from at least some of the plurality of pixels in a state in which the radiation is not emitted from the radiation source and a state in which the object is placed on the radiation detection panel;
- an arithmetic step of calculating a position of the object with respect to the radiation detection panel based on the first pixel signals; and
- a notification processing step of performing a notification process in a case in which the position of the object is out of a predetermined range.

17. A computer readable medium storing a radiography support program that supports imaging of an object with a radiography apparatus comprising a radiation detection panel in which a plurality of pixels are two-dimensionally arranged and which detects radiation emitted from a radiation source and the radiation source which irradiates the radiation detection panel with the radiation and causes a computer to perform:
- a first reading control step of reading first pixel signals from at least some of the plurality of pixels in a state in which the radiation is not emitted from the radiation source and a state in which the object is placed on the radiation detection panel;
- an arithmetic step of calculating a position of the object with respect to the radiation detection panel based on the first pixel signals; and
- a notification processing step of performing a notification process in a case in which the position of the object is out of a predetermined range.

* * * * *